United States Patent
Polt et al.

(10) Patent No.: US 11,504,325 B2
(45) Date of Patent: Nov. 22, 2022

(54) MICELLES AND VESICLES FOR THE DELIVERY OF GLYCOPEPTIDES

(71) Applicant: ARIZONA BOARD OF REGENTS ON BEHALF OF THE UNIVERSITY OF ARIZONA, Tucson, AZ (US)

(72) Inventors: Robin L. Polt, Tucson, AZ (US); Dillon Hanrahan, Tucson, AZ (US); Lajos Z. Szabo, Tucson, AZ (US); Michael L. Heien, Tucson, AZ (US); Chenxi Liu, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 297 days.

(21) Appl. No.: 16/637,671

(22) PCT Filed: Aug. 9, 2018

(86) PCT No.: PCT/US2018/046078
§ 371 (c)(1),
(2) Date: Feb. 7, 2020

(87) PCT Pub. No.: WO2019/032877
PCT Pub. Date: Feb. 14, 2019

(65) Prior Publication Data
US 2021/0361572 A1 Nov. 25, 2021

Related U.S. Application Data

(60) Provisional application No. 62/543,362, filed on Aug. 9, 2017.

(51) Int. Cl.
*A61K 8/11* (2006.01)
*A61K 8/14* (2006.01)
(Continued)

(52) U.S. Cl.
CPC ............ *A61K 9/107* (2013.01); *A61K 38/018* (2013.01)

(58) Field of Classification Search
None
See application file for complete search history.

(56) References Cited

U.S. PATENT DOCUMENTS

2008/0207492 A1  8/2008  Polt et al.
2012/0244210 A1  9/2012  Shinohara et al.

FOREIGN PATENT DOCUMENTS

WO    WO2014152795 A2    9/2014

OTHER PUBLICATIONS

Sarker et al., Biochem., 2011, vol. 50, pp. 4867-4876. (Year: 2011).*
(Continued)

*Primary Examiner* — Brian Gulledge
(74) *Attorney, Agent, or Firm* — Nguyen Tarbet LLC

(57) ABSTRACT

Methods for quality control and optimizing the formation and characterization of micelles, vesicles or other aggregates are described herein. Pharmaceutically relevant peptides may be modified to form glycopeptide surfactants which form micelles or other aggregates with another surfactant. Glycopeptide and glycolipid surfactants can aggregate to form particles that enhance drug delivery. The glycopeptide surfactants may be drugs or pro-drugs which are delivered via the micelles or other aggregated structures.

13 Claims, 8 Drawing Sheets

(51) Int. Cl.
A61K 9/107 (2006.01)
A61K 38/01 (2006.01)

(56) References Cited

OTHER PUBLICATIONS

Sarker. M et al. Lung Surfactant Protein A (SP-A) Interactions with Model Lung Surfactant Lipids and an SP-B Fragment. Biochemistry. vol. 50, No. 22. May 9, 2011. pp. 4867-4876; abstract; p. 4867, col. 1, paragraph 2; p. 4868. col. 1. paragraph 1; p. 4869, figures 2-3; p. 4869. col. 2. paragraph 2.

Polt, R et al. Delta-Selective Glycopeptides Related to Enkephalin Produce Profound Analgesia with Reduced Side Effects in Mice. RTO HFM Symposium on ~Combat Casualty Care in Ground Based Tactical Situations: Trauma Technology and Emergency Medical Procedures, held in St. Pete Beach, USA, Aug. 16-18, 2004. pp. 32-1-32-14.

Szabo. LS et al. Preparation of S-glycoside surfactants and cysteine thioglycosides using minimally competent Lewis acid catalysis. Carbohydrate Research, vol. 422. Mar. 3, 2016, pp. 1-4; p. 1. col. 1, paragraph 1; p. 2. table 1.

Aplin, JD et al. Preparation, Properties, and Applications of Carbohydrate Conjugates of Proteins and Lipids. Critical Reviews of Biochemistry, vol. 10, No. 4, 1981, pp. 259-306; p. 260, figure 1a; p. 263, paragraph 4; p. 266, table 2.

\* cited by examiner

MICELLES AND VESICLES FOR THE DELIVERY OF GLYCOPEPTIDES

CROSS REFERENCE

This application is a 371 and claims benefit of PCT/US18/46078 filed Aug. 9, 2018, which claims benefit of U.S. Provisional Application No. 62/543,362, filed Aug. 9, 2017, the specification(s) of which is/are incorporated herein in their entirety by reference.

GOVERNMENT SUPPORT

This invention was made with government support under Grant No. CHE1339597, awarded by NSF, and Grant No. R01 NS091238 awarded by the National Institutes of Health. The government has certain rights in the invention.

FIELD OF THE INVENTION

The present invention relates to glycoprotein and lipoprotein co-surfactants, their formation of micelles and vesicles for glycopeptide delivery, and the characterization of said micelles and vesicles by Diffusion Ordered Spectroscopy (DOSY).

BACKGROUND OF THE INVENTION

Surfactants have a variety of applications in several industries including cleaning products, crop and food productions, cosmetics, medicine, mineral extraction, and many others. Most industrial surfactants are ionic, coming from sulphate and phosphate salts of fatty acids or other lipids. Glycopeptides are a natural variety of surfactants composed of a hydrophilic carbohydrate head group with a lipophilic tail.

A current pharmaceutical challenge is the development of safe and effective oral formulations for macromolecules, including peptides and proteins. Barriers to developing oral formulations for proteins and peptides include poor intrinsic permeability, lumenal and cellular enzymatic degradation, rapid clearance, and chemical instability in the gastrointestinal (GI) tract. Pharmaceutical approaches to address these barriers that have been successful with traditional small, organic drug molecules have not readily translated into effective peptide and protein formulations.

The general strategy of pharmaceutical delivery using micelles and vesicles is well known in the art. Encapsulation and diffusion of drugs and pro-drugs in and from micelles and vesicles have been widely studied and various surfactants have been synthesized for the formation of said micelles and vesicles. The present invention features novel surfactant compositions that form micelles and vesicles.

The formation of new micelles and vesicles for specific applications necessitates methods for their optimization. One especially informative metric of a micelle or vesicle is its diffusion coefficient. From this, properties such as the critical micelle concentration, particle radius, and aggregation number can be determined. Changes in the diffusion coefficient are indicative of how the system is changed.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a method of optimizing the formation of a micelle or vesicle. The invention also features a method of quality control for the formation of a micelle or vesicle and a method for delivery of a glycopeptide using a micelle or vesicle. Various pharmaceutically relevant peptides can be modified to form glycopeptides which may be easier to deliver to the therapeutic site. In one embodiment, these glycopeptides may either act intact as drugs. In an alternative embodiment, these glycopeptides may be designed for cleavage and release of the original peptide, such as a prodrug.

In some aspects, the method of optimizing a formation of a micelle or vesicle may comprise forming a first micelle or vesicle from two or more co-surfactants according to two or more parameters, characterizing the first micelle or vesicle using Diffusion Ordered Spectroscopy (DOSY) to determine a first diffusion coefficient, changing at least one of the parameters and forming a second micelle or vesicle, characterizing the second micelle or vesicle using Diffusion Ordered Spectroscopy (DOSY) to determine a second diffusion coefficient, and comparing the first and second diffusion coefficients to determine if the first or second micelle or vesicle is more optimal for a specific application. As a non-limiting example, the parameters may include a number of components, a selection of components, a ratio of components, a concentration of components, an order of component addition, a temperature, a mixing time, or a solvent system.

In other aspects, the method of quality control for the formation of a micelle or vesicle may comprise forming a micelle or vesicle from two or more co-surfactants, characterizing the micelle or vesicle using Diffusion Ordered Spectroscopy (DOSY) to determine a diffusion coefficient, and determining the quality of the micelle or vesicle by comparing the diffusion coefficient to an optimal range of diffusion coefficients for a specific application.

In some embodiments, the first co-surfactant comprises a glycopeptide and the second co-surfactant comprises a glycolipid. The glycopeptides may comprise a peptide linked to a saccharide. The glycolipid may be according to any of the following structures:

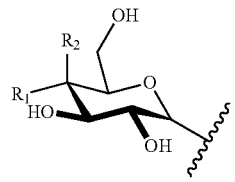

Glc: $R_1$ = OH, $R_2$ = H
Gal: $R_1$ = H, $R_2$ = OH
Cel: $R_1$ = O-β-D-Glc, $R_2$ = H
Lac: $R_1$ = O-β-D-Gal, $R_2$ = H
Mal: $R_1$ = O-α-D-Glc, $R_2$ = H

α and β (1:1)

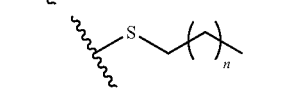

β only

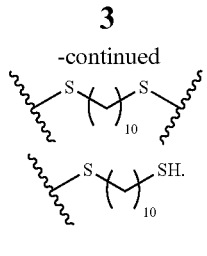

n = 6, 8, 10

The first co-surfactant and the second co-surfactant can aggregate to form said micelle or vesicle. The micelle or vesicle can be used in a glycopeptide delivery system.

One of the unique and inventive technical features of the present invention is that the diffusion coefficient of the micelle or vesicle is determined by DOSY. Without wishing to limit the invention to any theory or mechanism, it is believed that the technical feature of the present invention advantageously provides optimization or quality control of a micelle or vesicle formed from glycopeptide and glycolipid co-surfactants. None of the presently known prior references or work has the unique inventive technical feature of the present invention.

Another unique and inventive technical features of the present invention is that the glycopeptide to be delivered functions as a co-surfactant. Without wishing to limit the invention to any theory or mechanism, it is believed that the technical feature of the present invention advantageously provides for micelle or vesicle formation with incorporation of the glycopeptide and subsequent effective drug delivery. None of the presently known prior references or work has the unique inventive technical feature of the present invention.

BRIEF DESCRIPTION OF THE DRAWINGS

The features and advantages of the present invention will become apparent from a consideration of the following detailed description presented in connection with the accompanying drawings in which.

DESCRIPTION OF PREFERRED EMBODIMENTS

Figure 2:
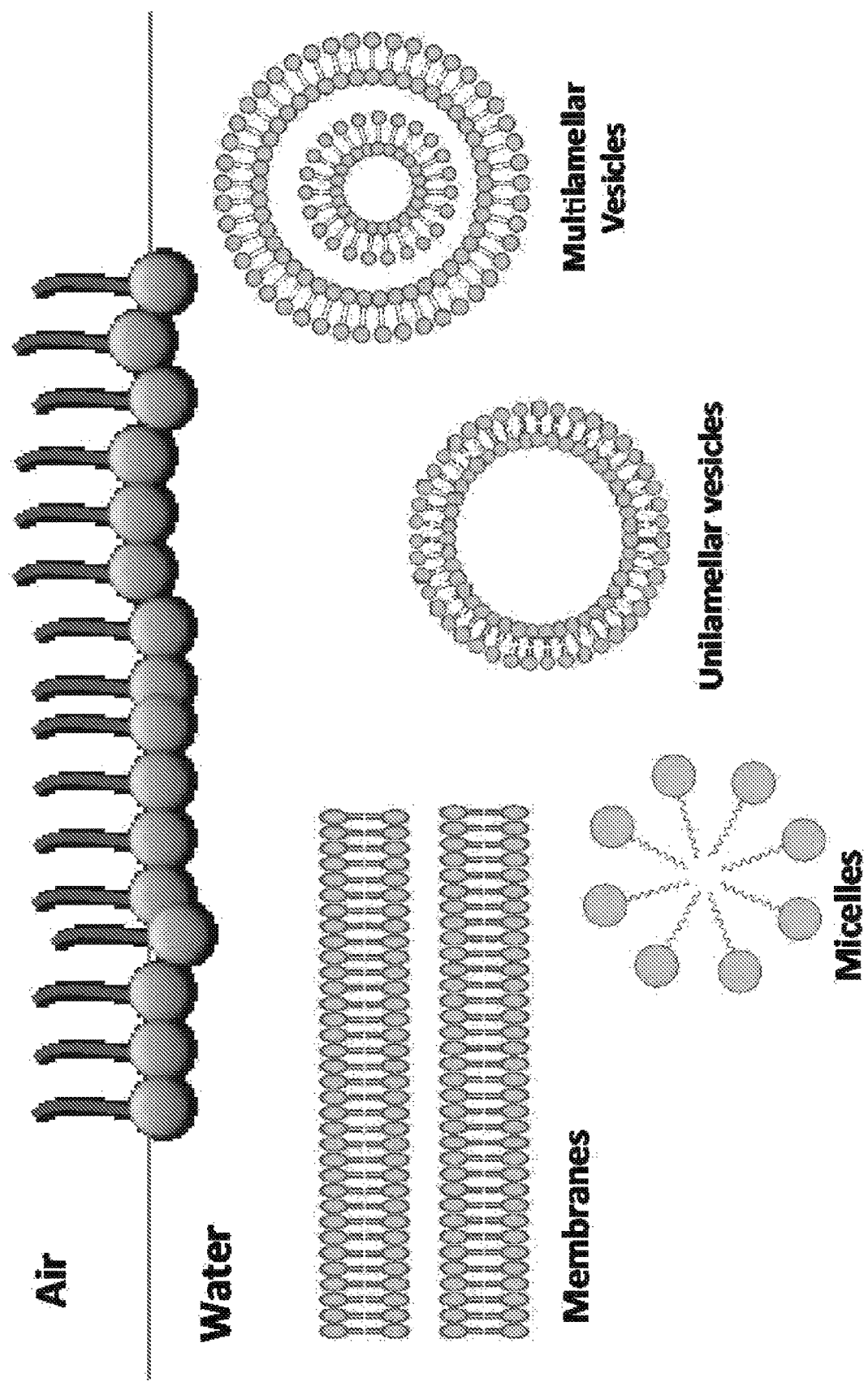
FIG. 2 shows an illustration of surfactant assembly architectures
Figure 3:
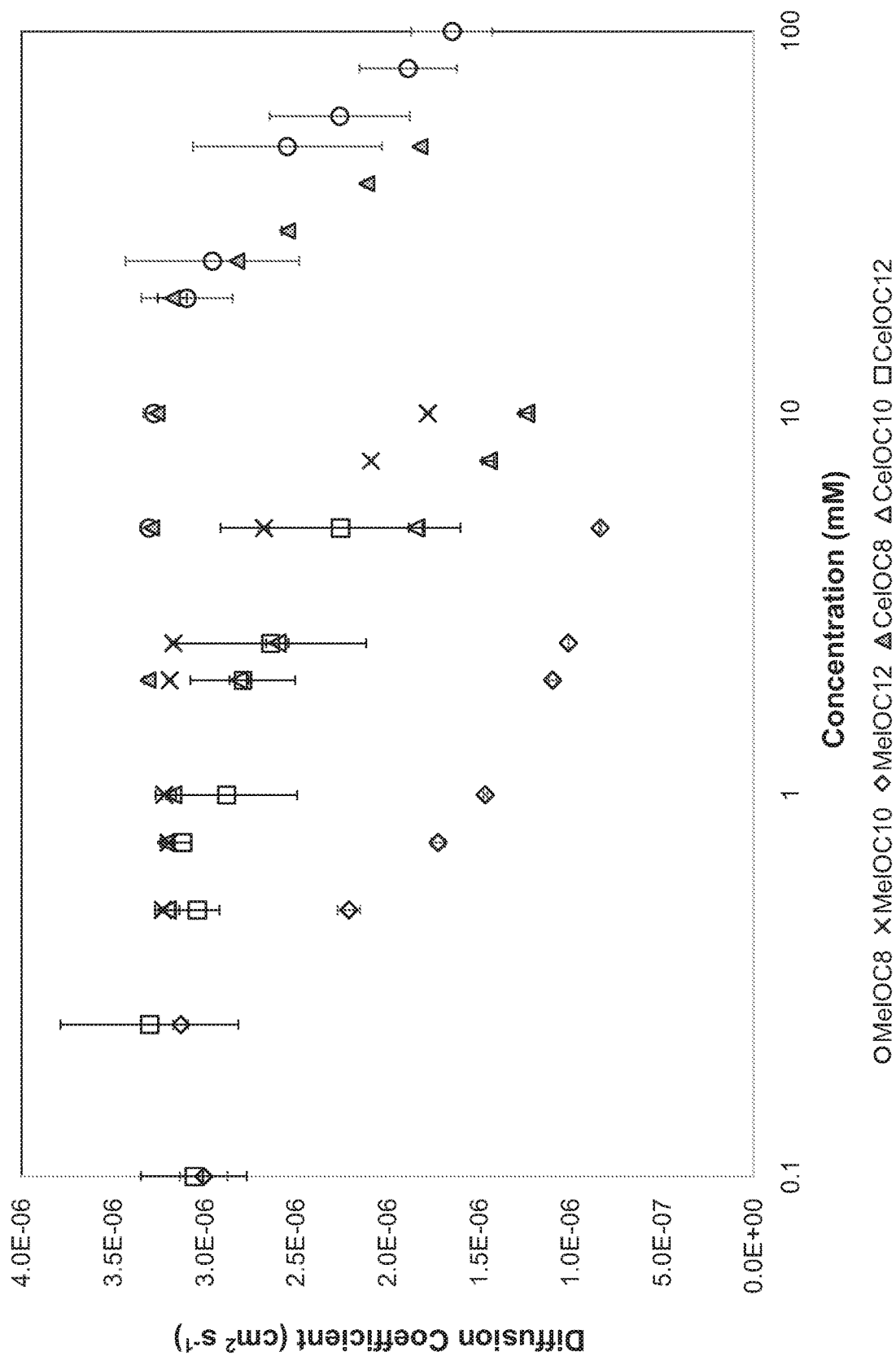
FIG. 3 shows a plot of diffusion coefficients vs. concentration for various glycolipids.
Figure 4A:
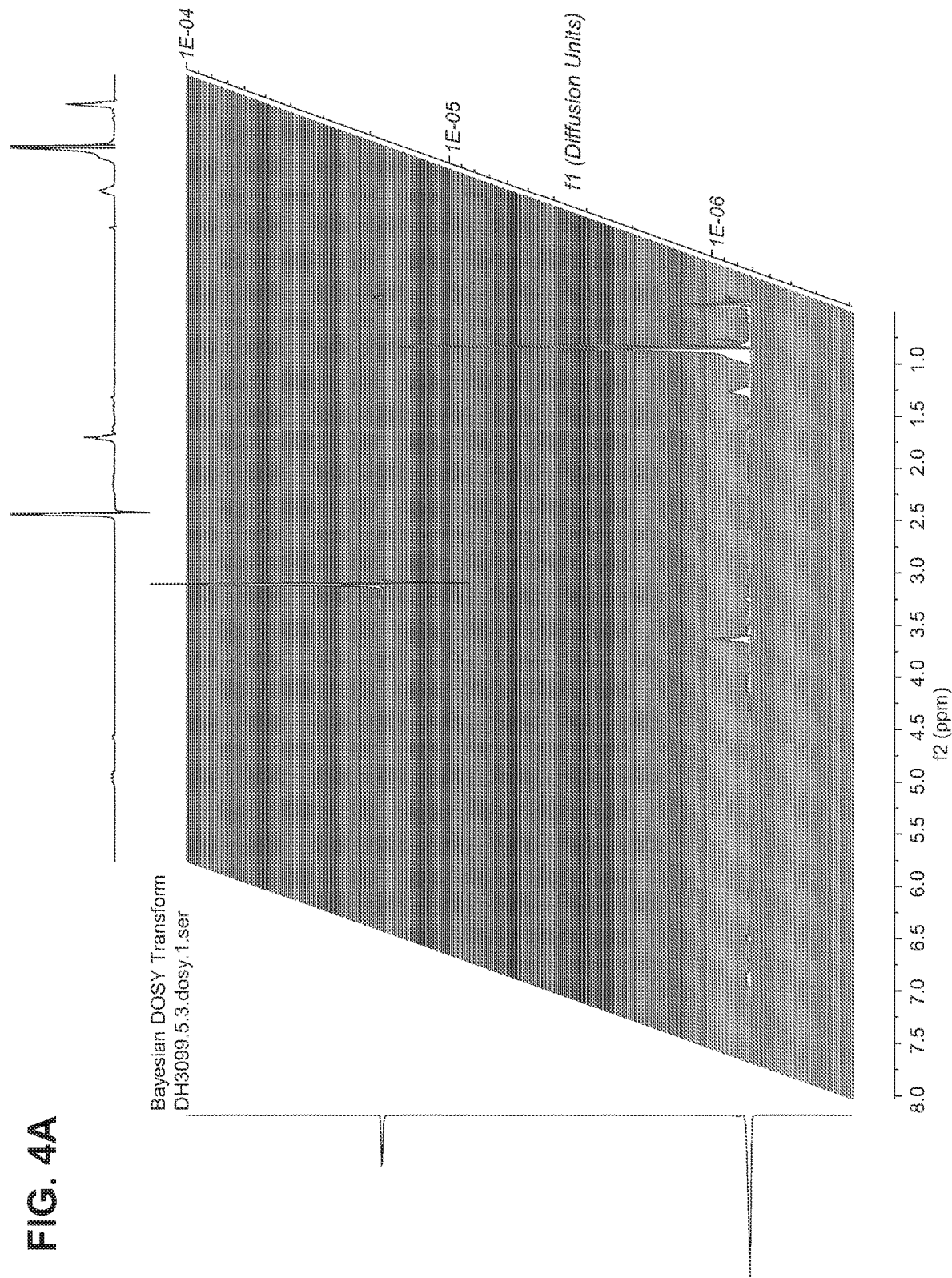
FIG. 4A shows a DOSY plot of diffusion coefficients of micelles formed from lactomorphin and SDS surfactants.
Figure 4B:
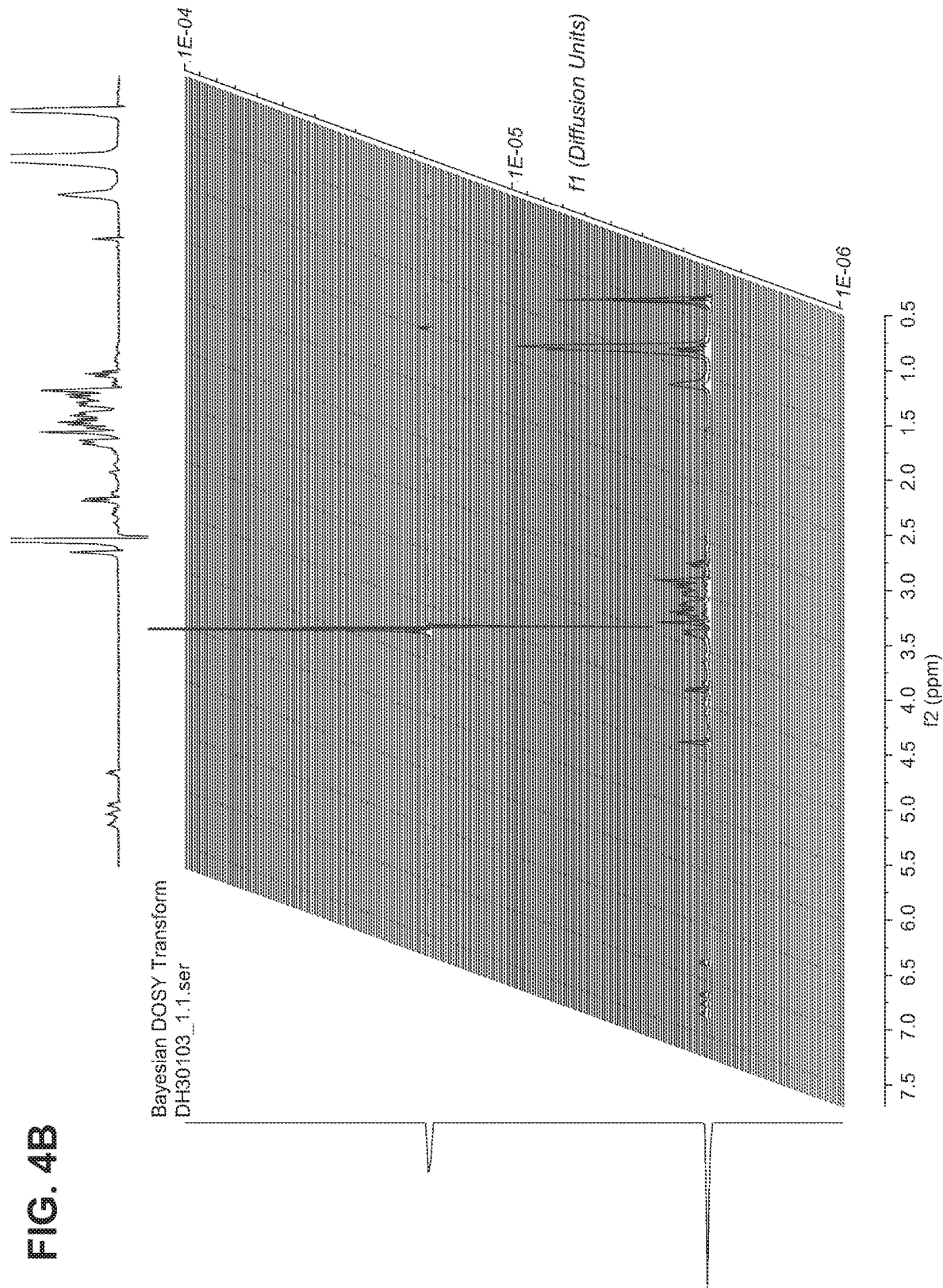
FIG. 4B shows a DOSY plot of diffusion coefficients of micelles formed from lactomorphin and octyl glucoside surfactants.
Figure 5A:
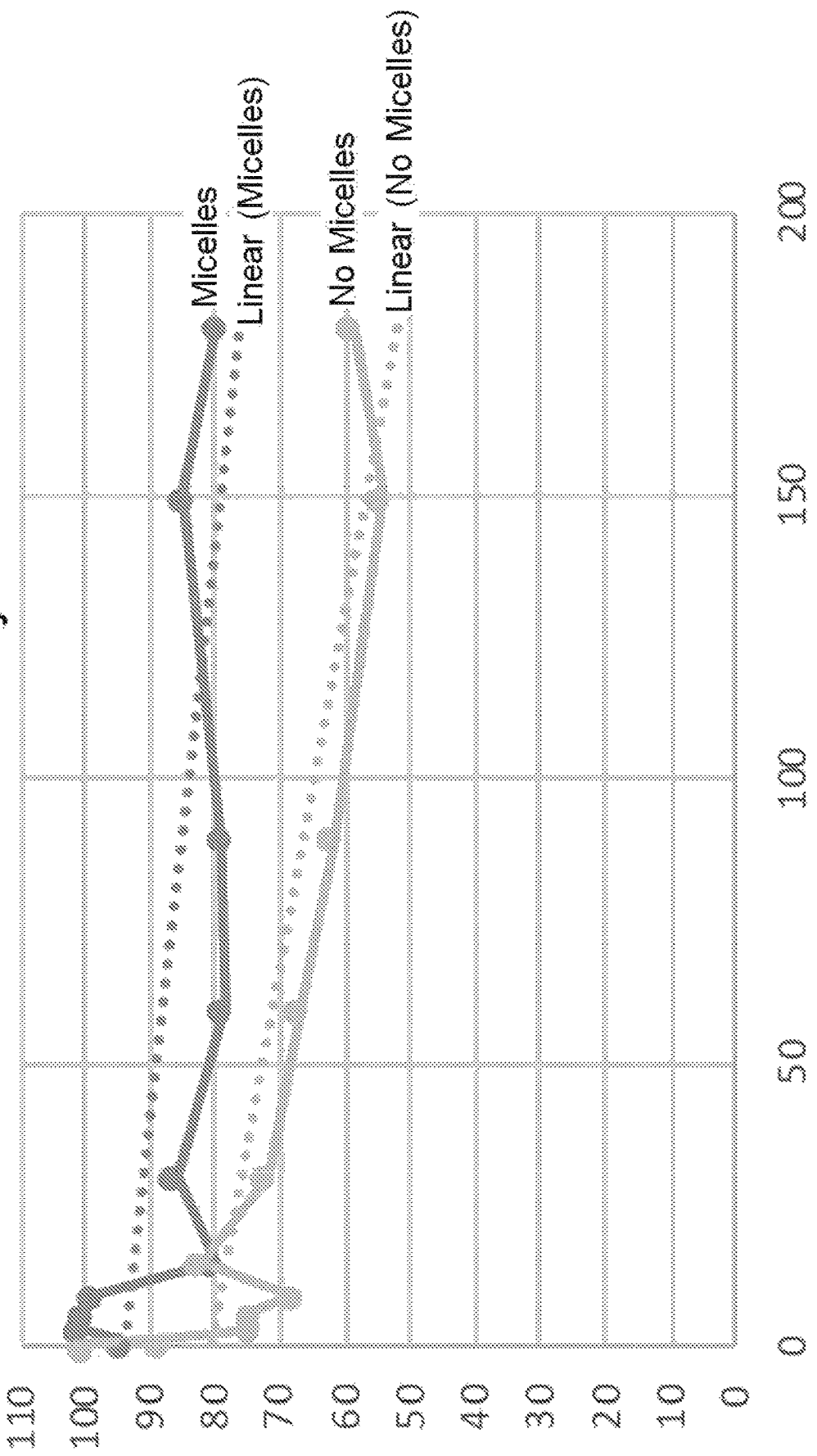
FIG. 5A shows the percentage of MMP-2200 remaining in 0.1% trifluoroacetic acid in water over time (minutes) in the presence and absence of dodecylglucoside. The normalized signal (percent) is plotted vs. time (minutes). The micelles show a slower rate of degradation when compared to the control in water.
Figure 5B:
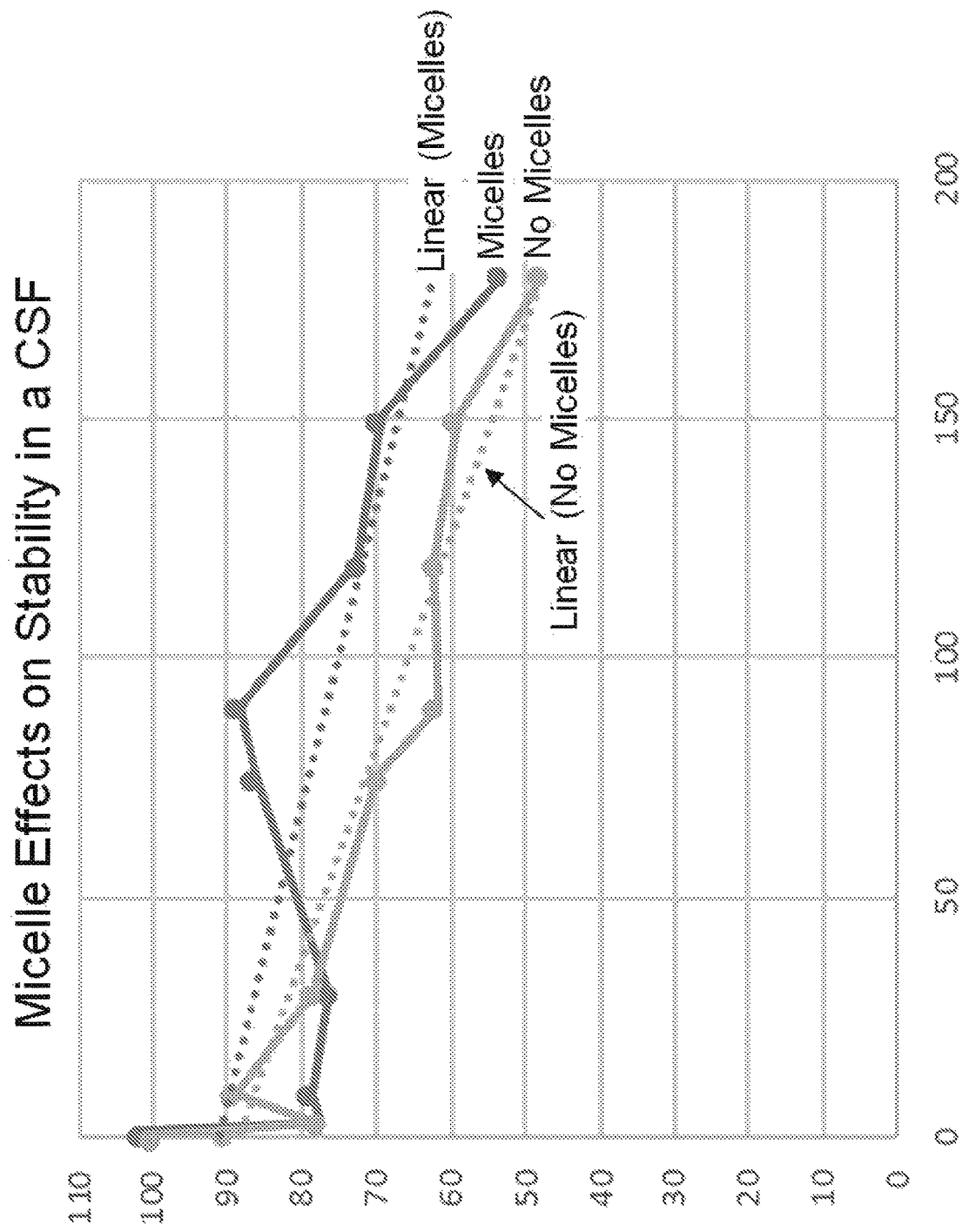
FIG. 5B shows the percentage of MMP-2200 remaining in artificial CSF over time (minutes) in the presence and absence of dodecylglucoside. The normalized signal (percent) is plotted vs. time (minutes). The micelles show a slower rate of degradation when compared to the control in CSF.

In preferred embodiments, the present invention features the use of diffusion-ordered spectroscopy (DOSY) to observe the diffusion of surfactant molecules and aggregates to characterize surfactant properties such as the critical micelle concentration, particle radius, and aggregation number. As used herein, the term "glycoaggregate" refers to a collection or aggregation of glycosidic molecules, preferably forming micelles or vesicles, as shown in FIG. 2. Further, multicomponent micellular solutions, such as a micellular solution with a lipid or co-surfactant added or a solution with nonpolar solvents containing inverse micelles, may be characterized with DOSY.

According to some embodiments, the present invention features a method of optimizing formation of a glycoaggregate. The method may comprise forming a first glycoaggregate from at least two co-surfactants according to two or more reaction parameters, characterizing the first glycoaggregate using Diffusion Ordered Spectroscopy (DOSY) to determine a first diffusion coefficient, modifying at least one of the reaction parameters, forming a second glycoaggregate from at least two co-surfactants according to the modified reaction parameters, characterizing the second glycoaggregate using DOSY to determine a second diffusion coefficient, and comparing the first and second diffusion coefficients to determine if the first glycoaggregate or the second glycoaggregate is more suitable for a specific application, such as drug delivery. In some embodiments, the at least two co-surfactants may comprise a glycopeptide and a lipid. In one embodiment, the first glycoaggregate may be a micelle or vesicle. In another embodiment, the second glycoaggregate may be a micelle or vesicle. For comparison, both the first glycoaggregate and the second glycoaggregate should be micelles, or vesicles, but not one of each.

According to other embodiments, the present invention features a method of quality control for the formation of a glycoaggregate. The method may comprise forming the glycoaggregate from at least two co-surfactants, characterizing the glycoaggregate using Diffusion Ordered Spectroscopy (DOSY) to determine a diffusion coefficient, and comparing the diffusion coefficient to an optimal range of diffusion coefficients for a specific application to determine a quality of the glycoaggregate. In one embodiment, the glycoaggregate may be a micelle or vesicle.

In some embodiments, examples of the reaction parameters include a number of the co-surfactants, a selection of the co-surfactants, a ratio of the co-surfactants, a concentration of the co-surfactants, an order of addition of the co-surfactants, a reaction temperature, a mixing time, a presence of a catalyst, and a type of solvent system. By varying any one of these parameters, while fixing the others, the diffusion coefficients of the glycoaggregates can be compared to determine suitability in the specific application.

According to some other embodiments, the present invention features a method of quality control for the formation of a glycoaggregate. The method may comprise forming the glycoaggregate from at least two co-surfactants, characterizing the glycoaggregate using Diffusion Ordered Spectroscopy (DOSY) to determine a diffusion coefficient, and comparing the diffusion coefficient to an optimal range of diffusion coefficients for a specific application to determine a quality of the glycoaggregate. In one embodiment, the glycoaggregate may be a micelle or vesicle.

Consistent with the method the methods described herein, in some embodiments, the first co-surfactant may comprise a glycopeptide. The glycopeptide may be a drug or a pro-drug. As a non-limiting example, the glycopeptide may be a glycosylated opioid peptide or lactomorphin. Without wishing to limit the present invention, the glycopeptides may be used in the treatment of levodopa-induced dyskinesia. For example, the glycopeptides may be used in the treatment of Parkinson's disease.

According to one embodiment, a specific application of the glycoaggregate may be drug delivery. Without wishing to limit the invention to any particular theory or mechanism, it can be advantageous for glycopeptide delivery for the glycopeptide to function as a co-surfactant in the formation of a micelle or vesicle. In selected embodiments, the delivery system or delivery vehicle may deliver the glycopeptide to a therapeutic site.

In another embodiment, the delivery system or delivery vehicle may comprise a microemulsion or a nanoparticle. In some embodiments, the vesicle may be a unilamellar vesicle or a multilamellar vesicle. In other embodiments, the micelle or vesicle may have a diameter of about 5-7 nm. In further embodiments, a diffusion coefficient of the micelle or vesicle may be determined using Diffusion Ordered Spectroscopy (DOSY).

In some embodiments, the glycopeptide can be synthesized by providing a peptide, providing a saccharide, and covalently linking the peptide with the saccharide, thereby forming said glycopeptide. In a non-limiting example, the peptide includes a serine residue, which is linked to the saccharide. An example of the saccharide is a glucose. The peptide itself may be a drug or a pro-drug. It is believed that this strategy may be used to modify pharmaceutically relevant peptides to form the glycopeptides, which may be advantageously delivered by a micelle or vesicle.

In other embodiments, the second co-surfactant may comprise a glycolipid. In one embodiment, the glycolipid may be a saccharide linked to a chain component. For example, the glycolipid may be according to the following structures: i) the saccharide portion may be according to the following formula:

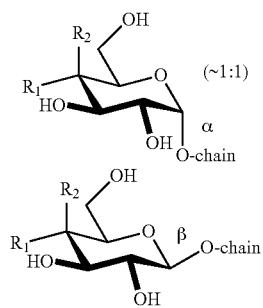

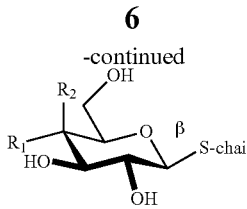

i) $R_1$ = H, O——H, O-β-D-Glucose, O-β-D-Galactose, or O-α-D-Glucose
$R_2$ = H or OH In some embodiments, the chain may be according to any one of the following formulas:

α and β
(1:1)

β only

β only

β only where n is 6, 8, or 10.

As shown above, the glycolipids may comprise glucosides and thioglucosides which form micelles in aqueous solution. The aglycones may comprise long-chained fatty alcohols or thiols. The alpha,omega-thiols contain additional thiols that can be glycosylated a second time at the omega SH to produce boloform amphiphiles, adsorbed to metal surfaces, or extended via a disulfide linkage (~S—S~).

In some other embodiments, the second co-surfactant may comprise another lipid, which may or may not be pharmacologically active. In some embodiments, the additional lipids may be simple lipids that increase the robustness of the micelles, or may be used to impart a positive or negative charge to the micelles. The lipids may also have specific cellular recognition elements such as those found on glycospingolipids and gangliosides. As a non-limiting example, the second co-surfactant may be according to any one of the following structures:

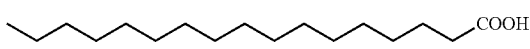

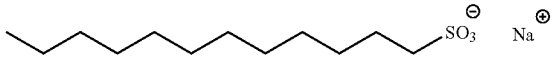

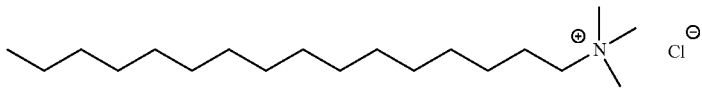

-continued

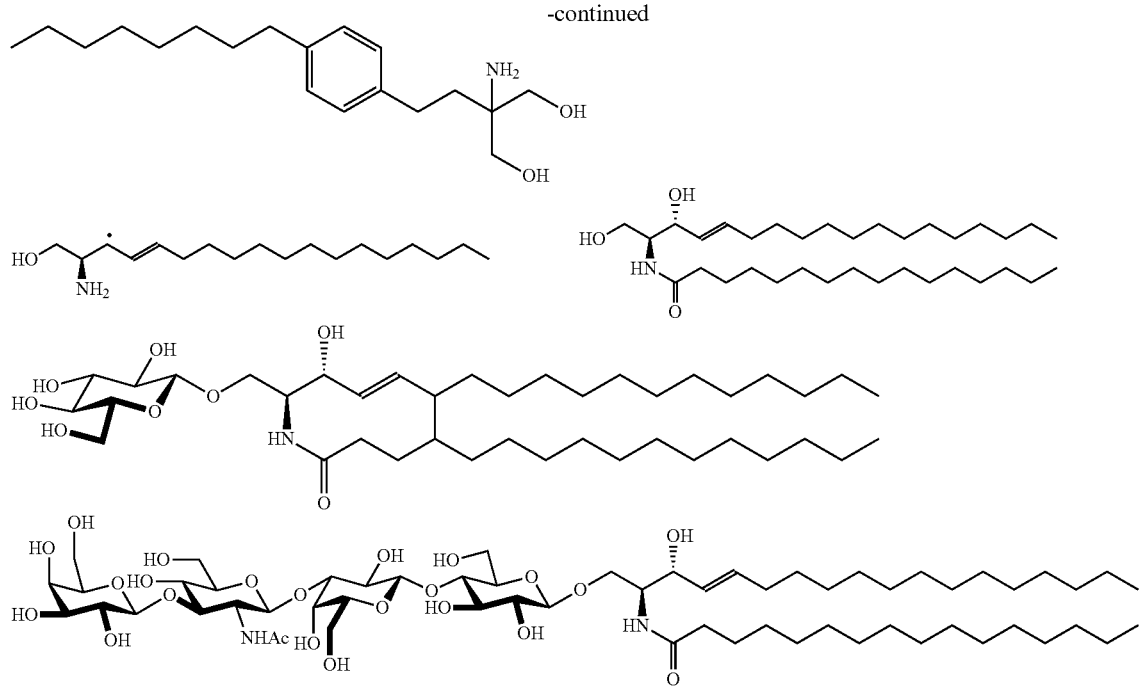

Figure 1A:
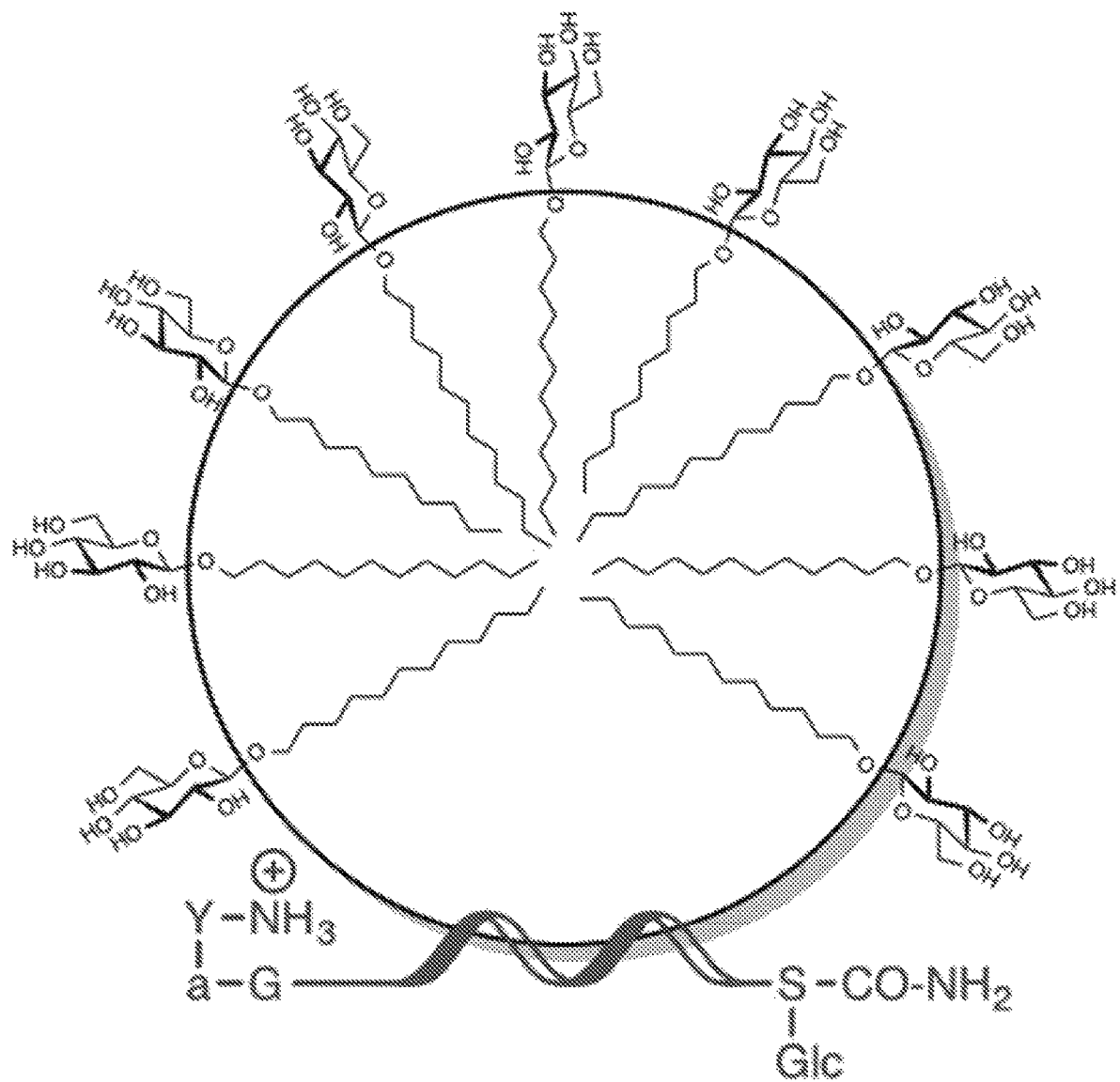
FIG. 1A shows a schematic of a micelle formed from glycolipids and glycopeptides

According to other embodiments, the present invention features a glycopeptide delivery system comprising a glycolipid aggregate. Referring to FIG. 1A, in one embodiment, the glycolipid aggregate may comprise a first co-surfactant comprising a glycopeptide, and a second co-surfactant comprising a lipid. The glycopeptides may be according to those described herein. Consistent with previous embodiments, the lipids may be glycolipids or additional lipids such as those described herein. Without wishing to be bound to a particular mechanism, the first co-surfactant and the second co-surfactant can aggregate to form said glycoaggregate. The glycoaggregate may be a micelle or vesicle. In some embodiments, the vesicle may be a unilamellar vesicle or a multilamellar vesicle. Preferably, the glycoaggregate has a diffusion coefficient that is determined using Diffusion Ordered Spectroscopy (DOSY).

Figure 1B:
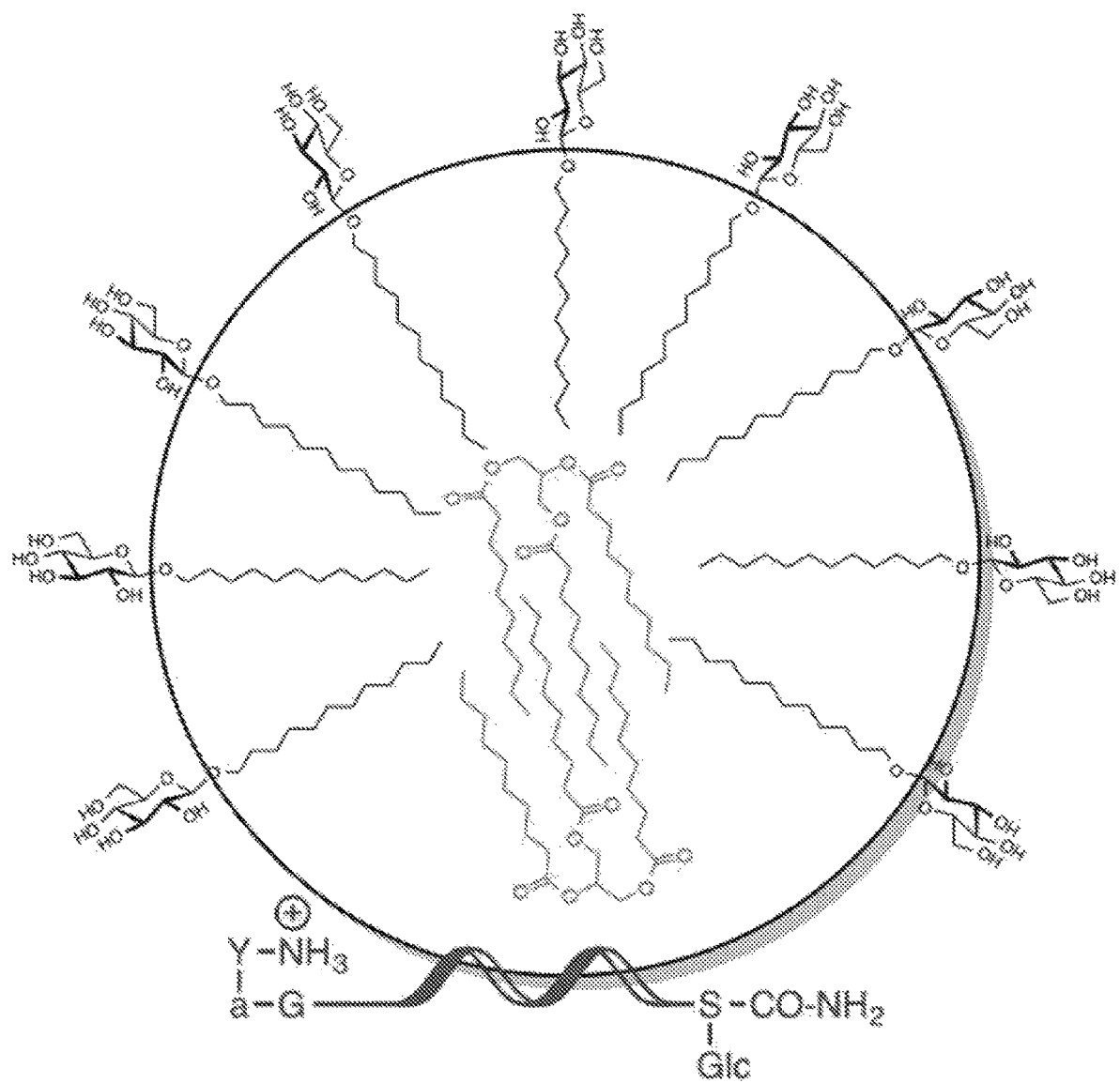
FIG. 1B shows a schematic of a triglyceride encapsulating micelle formed from glycolipids and glycopeptides

Referring to FIG. 1B, in other embodiments, the glycoaggregate may further comprise lipid molecules, such as triglycerides. In a non-limiting embodiment, the co-surfactants can aggregate to form a lipid shell that encapsulates the lipid molecules.

In some embodiments, the glycoaggregate can have a diameter of ranging from about 5 to about 50 nm. For example, the glycoaggregate diameter may be about 5-7 nm. In other embodiments, the glycoaggregate can have a diameter larger than 50 nm. For instance, if glycoaggregate includes encapsulated lipid molecules, the glycoaggregate diameter may be about 100-500 nm.

In some embodiments, the delivery system may be in the form of nanoparticles or microemulsion. Without wishing to limit the present invention to a particular theory or mechanism, the delivery system is configured to deliver the glycopeptide to a therapeutic site.

In some embodiments, the present invention features a catalytic, multi-gram scale synthesis of alkyl glycosides with minimally-competent Lewis acids which may allow for the production of a library of fundamental glycolipids for structure and function studies.

TABLE 1

Surface tension and DOSY diffusion coeficiants for various glycolipids. CMC (mM)

| Compound | Surface Tens. | DOSY (Diffusion Coefficients) |
| --- | --- | --- |
| MelOC8 | 44 ± 5 | 40 ± 5 |
| MelOC10 | 3.3 ± 0.2 | 3.9 ± 0.1 |
| MelOC12 | 0.30 ± 0.02 | 0.31 ± 0.005 |
| CelOC8 | 19 ± 3 | 21 ± 2 |
| CelOC10 | 1.8 ± 0.2 | 2.2 ± 0.7 |
| CelOC12 | 0.18 ± 0.01 | 0.29 ± 0.4 |
| GlcOC8 | 20 (lit) | 20 ± 3 |
| GlcOC10 | 2.2 (lit) | 2.1 ± 0.7 |
| SDS | 8.2 (lit) | 8.4 ± 2 |

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of optimizing formation of a glycoaggregate, the method comprising:
   a. forming a first glycoaggregate from at least two co-surfactants according to two or more reaction parameters, wherein the at least two co-surfactants comprises a glycopeptide and a lipid;
   b. characterizing the first glycoaggregate using Diffusion Ordered Spectroscopy (DOSY) to determine a first diffusion coefficient;
   c. modifying at least one of the reaction parameters;
   d. forming a second glycoaggregate from at least two co-surfactants according to the modified reaction parameters, wherein the at least two co-surfactants comprises a glycopeptide and a lipid;
   e. characterizing the second glycoaggregate using DOSY to determine a second diffusion coefficient; and
   f. comparing the first and second diffusion coefficients to determine if the first glycoaggregate or the second glycoaggregate is more suitable for a specific application, wherein the specific application is drug delivery.

2. The method of claim 1, wherein the first glycoaggregate is a micelle or vesicle.

3. The method of claim 1, wherein the second glycoaggregate is a micelle or vesicle.

4. The method of claim 1, wherein the reaction parameters are selected from the group comprising a number of the co-surfactants, a selection of the co-surfactants, a ratio of the co-surfactants, a concentration of the co-surfactants, an order of addition of the co-surfactants, a reaction temperature, a mixing time, a presence of a catalyst, and a type of solvent system.

5. The method of claim 1, wherein the glycopeptide is a drug or a pro-drug.

6. The method of claim 1, wherein the glycopeptide is synthesized by providing a peptide, providing a saccharide, and covalently linking the peptide with the saccharide, thereby forming said glycopeptide.

7. The method of claim 6, wherein the peptide includes a serine residue, wherein the saccharide is linked to the serine residue.

8. The method of claim 6, wherein the saccharide is a glucose.

9. The method of claim 6, wherein the peptide is a drug or a pro-drug.

10. The method of claim 1, wherein the glycopeptide is a glycosylated opioid peptide.

11. The method of claim 1, wherein the glycopeptide is lactomorphin.

12. The method of claim 1, wherein the lipid is a glycolipid according to any one of the following structures:

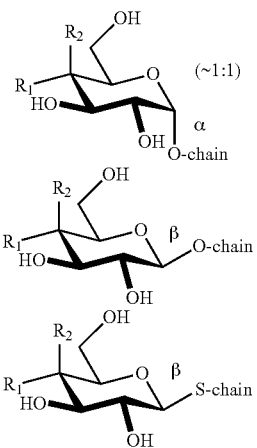

wherein $R_1$ is H, OH, O-β-D-Glucose, O-β-D-Galactose, or O-α-D-Glucose;

wherein $R_2$ is H or OH;

wherein the chain is according to any one of the following formulas:

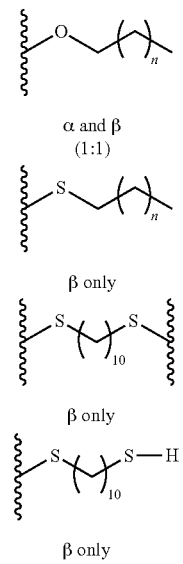

wherein n is 6, 8, or 10.

13. The method of claim 1, wherein the lipid is according to any one of the following structures:

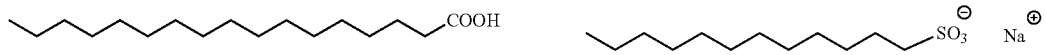

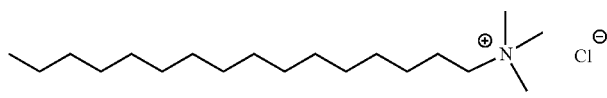

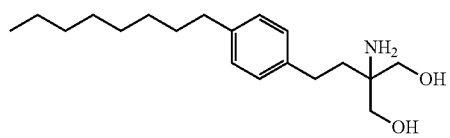

-continued
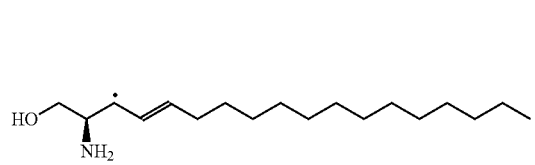
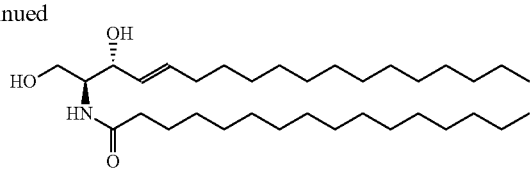
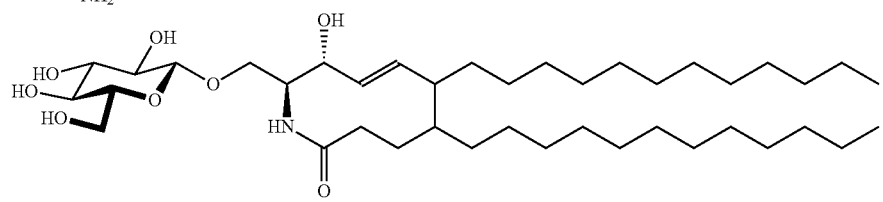
, or
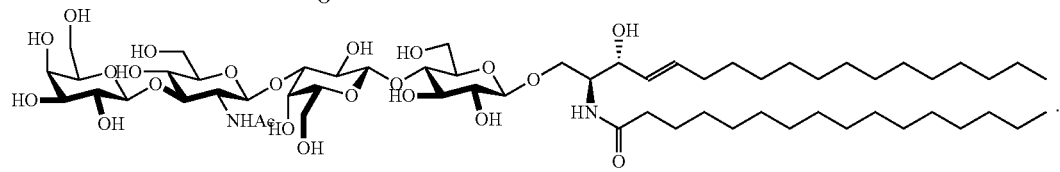
.
* * * * *